United States Patent
Shang et al.

(10) Patent No.: US 9,539,024 B2
(45) Date of Patent: Jan. 10, 2017

(54) DISPOSABLE CIRCUMCISION ANASTOMAT

(76) Inventors: Jianzhong Shang, Wuhu (CN);
Jingjing Shang, Wuhu (CN)

( * ) Notice: Subject to any disclaimer, the term of this patent is extended or adjusted under 35 U.S.C. 154(b) by 225 days.

(21) Appl. No.: 13/814,478

(22) PCT Filed: Aug. 19, 2011

(86) PCT No.: PCT/CN2011/001385
§ 371 (c)(1),
(2), (4) Date: Feb. 5, 2013

(87) PCT Pub. No.: WO2012/022124
PCT Pub. Date: Feb. 23, 2012

(65) Prior Publication Data
US 2013/0144304 A1 Jun. 6, 2013

(30) Foreign Application Priority Data
Aug. 19, 2010 (CN) ...................... 2010 2 0297600 U

(51) Int. Cl.
*A61B 17/326* (2006.01)
*A61B 17/00* (2006.01)

(52) U.S. Cl.
CPC ...... *A61B 17/326* (2013.01); *A61B 2017/0023* (2013.01)

(58) Field of Classification Search
CPC ............... A61B 17/326; A61B 2017/0023; A61B 17/11; A61B 17/1114; A61B 2017/1107; A61B 2017/1121; A61B 2017/1132; A61B 2017/1135; A61B 2017/1139
USPC .......................................... 606/118, 151, 153
See application file for complete search history.

(56) References Cited

U.S. PATENT DOCUMENTS

| | | | | |
|---|---|---|---|---|
| 3,111,124 | A * | 11/1963 | Rodbard | 606/118 |
| 3,612,057 | A * | 10/1971 | Freedman | 606/118 |
| 4,491,136 | A * | 1/1985 | LeVeen | 606/118 |
| 5,163,943 | A * | 11/1992 | Mohiuddin et al. | 606/118 |
| 5,797,921 | A * | 8/1998 | Cimini et al. | 606/118 |
| 8,777,962 | B1 * | 7/2014 | Poplin | A61B 17/326 606/118 |
| 2008/0154283 | A1 * | 6/2008 | Shang | 606/118 |
| 2009/0005722 | A1 * | 1/2009 | Jennlngs-Spring | 604/20 |

FOREIGN PATENT DOCUMENTS

CN WO 2005039424 A1 * 5/2005 ........... A61B 17/326

OTHER PUBLICATIONS

English Translation of WO 2005/039424 A1.*

* cited by examiner

*Primary Examiner* — Ryan J Severson
*Assistant Examiner* — Christian Knauss
(74) *Attorney, Agent, or Firm* — Gokalp Bayramoglu

(57) ABSTRACT

A disposable circumcision anastomat comprises an internal ring (2) and an external ring (1) having an opening (10). The internal ring (2) substantially matches an external ring (1). The external ring (1) includes a sidewall (100). The sidewall (100) is provided with a retainer (7) for holding a gasket. The retainer (7) is an annular ring (71) extended inwardly from the sidewall (100) of the external ring. The annular ring (71) is equipped with an opening (710), corresponding to opening (10) on the external ring. The width (K1) of the annular ring is less than the width (K2) of the blade. The anastomat is safe, reliable, and able to reduce pain experienced by patients after surgery.

14 Claims, 7 Drawing Sheets

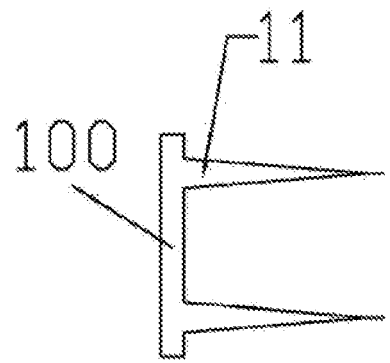
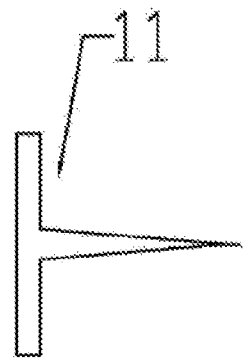
Fig 3    Fig 4
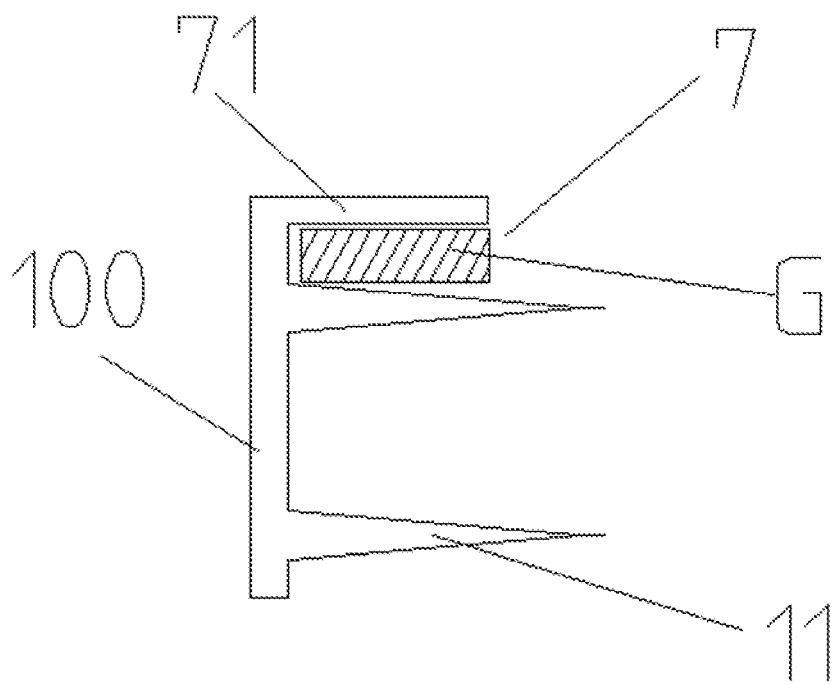
Fig. 5

DISPOSABLE CIRCUMCISION ANASTOMAT

CROSS REFERENCE TO RELATED APPLICATIONS

This application is the national stage of PCT application serial number PCT/CN2011/001385, filed on Aug. 19, 2011, which claims priority to Chinese application serial number 201020297600.6, filed on Aug. 19, 2010, the entire contents of which are incorporated herein.

BACKGROUND

Field of the Invention

The invention relates to a type of medical apparatus, especially a type of disposable circumcision anastomat.

Related Art

Redundant prepuce or phimosis is one of the reasons for male urinary system infection and aggravation of sexually transmitted diseases. Redundant prepuce or phimosis can cause urinary tract infection that may lead to chronic prostatitis, which presents as a series of symptoms such as back pain, impotence and prospermia. In addition, the effect of male circumcision has been widely recognized in reducing the transmission HIV. Therefore, removing redundant foreskin or phimosis is a good way to prevent and/or arrest these diseases.

One of the inventors of the present invention, Mr. Jianzhong Shang, has been credited by some authorities as having created key products and technologies in the field of circumcision. The development of circumcision apparatuses has now entered a new stage of design and promotion.

The inventors of the present invention have conducted numerous tests and research in the field of circumcision technology and have applied for many patents relating thereto. Present circumcision devices are shown in FIG. 1 to FIG. 4, as a disposable circumcision apparatus comprising an internal ring 2 and external ring 1 having an opening 10 that matches each other. The external ring 1 has a side wall 100 and a blade 11, the blade comprising a single, dual, or multi-blade structure. This disposable circumcision apparatus has revolutionized the industry, bestowing benefits such as safety, minimal invasion, simplicity, beauty, and a high degree of standardization.

The present technology, however, may cause discomfort to patients, as they are required to wear the device shown in FIGS. 1-4 for several days after circumcision surgery. Anesthetic drugs meant to relieve pain after the surgery wear off after only a few hours. Typically, patients feel pain due to the incision on the prepuce. Additionally, the incision may become easily infected when from wearing the present technology after surgery. It would be beneficial, then, to increase the sterility of the apparatus.

SUMMARY

The main purpose of this invention is to overcome the deficiencies of existing circumcision devices and to provide a safer, cleaner, and more convenient disposable circumcision anastomat.

In order to realize the above-mentioned goals, this invention adopts a technical solution as follows: A disposable circumcision anastomat comprises an internal ring and external ring having an opening, the internal ring sized and shaped to be placed inside the external ring, the external ring including a sidewall that is connected to a blade. An annular ring is placed on top of the sidewall, thereby forming an annular retaining space between the annular ring and the blade. A gasket may be placed into the annular retaining space.

In one embodiment, the annular ring is in the shape of a mechanical washer, e.g., a circular disk with a hole. The width of the ring extends inwardly from the sidewall of the external ring, the annular ring comprising an opening which corresponds to the opening on the external ring. The width of the annular ring is generally less than the width of the annular blade.

In another embodiment, the retainer comprises a number of tabs extended inwardly from the sidewall of the external ring, the length of the tabs generally less than the width of the blade. The tabs and the adjacent blade form a retainer for holding a gasket.

In one embodiment, the annular ring or tabs may be connected to the sidewall via a snap-in joint structure.

The joint structure comprises a male connection part extending from the annular ring or tabs and a receiving female connection formed at least partially through the sidewall. In another embodiment, these structural elements may be reversed, in other words, the annular ring comprising a receiving cavity and the sidewall comprising the male connection part.

In one embodiment, the male connection part comprises a pin and the female connection comprises a hole or cavity sized and shaped to receive the male connection part snugly.

In one embodiment, the retainer comprises a circular sheet, e.g., a circular ring extended from the exterior verge of the circular sheet, the circular ring fitted to either cover the outside circumference of the sidewall or abut the interior circumference of the sidewall of the external ring, the width of the ring typically less than the width of the blade.

Both the circular ring and the sidewall of the external ring may comprise screw threads so that they may be connected to one another by one or more screws.

In one embodiment, the gasket is typically made from absorbent materials.

In another embodiment, the gasket is typically made from non-woven fabrics, cotton, or sponge material.

In yet still another embodiment, the gasket is typically made of non-woven fabrics, cotton, or sponge material having an anesthetic drug introduced into the sponge material.

The beneficial effects of the invention are as follows:

1. The circular ring and the blade form an annular holding space for retaining a gasket. The gasket can be made of non-woven fabrics, cotton, sponge, or any other absorbent material so that it may retain an anesthetic drug. The anesthetic drug reduces pain that patients generally experience after surgery. This disposable circumcision apparatus is more comfortable, more reliable and safer that prior art models because of this pain-relieving property.

2. The retainer may comprise an annular sheet similar to a mechanical washer, two or more tabs or hooks extended inwardly from the sidewall of the external ring, or a circular sheet with a circular ring. Patients have various options for choosing different kinds of disposable circumcision apparatus.

3. The hinged structure generally makes the apparatus more convenient to operate.

BRIEF DESCRIPTION OF THE DRAWINGS

FIGS. 3 and 4 illustrate the cross-section of an external ring of the anastomat of FIGS. 1 and 2.

FIG. 5 illustrates a cross-section of an external ring used in a first embodiment of a disposable circumcision anastomat in accordance with the teachings herein.

DETAILED DESCRIPTION

Figure 1:
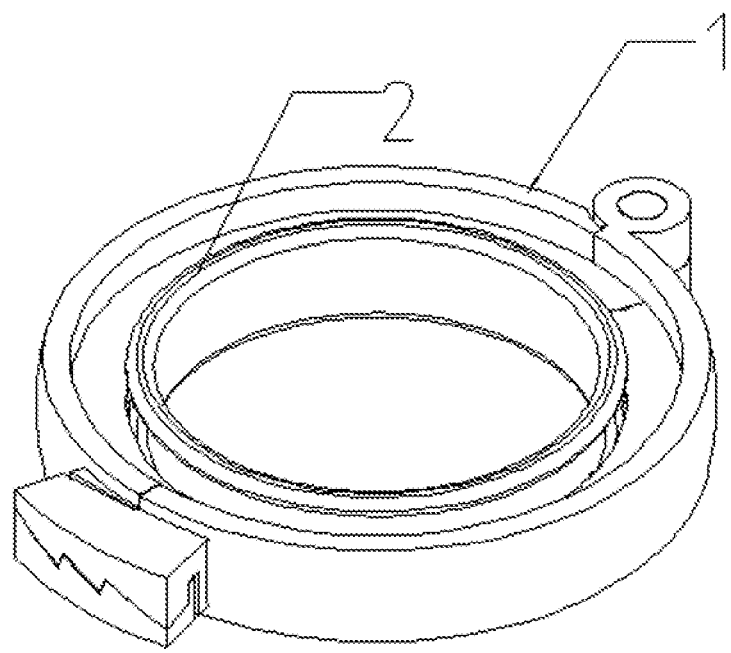
FIG. 1 illustrates one embodiment of a disposable circumcision anastomat in the prior art.
Figure 2:
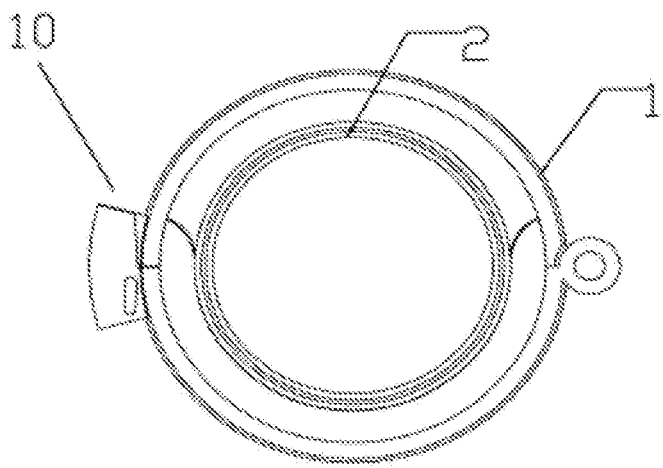
FIG. 2 illustrates a front view of the disposable circumcision anastomat of FIG. 1.

The present invention relates to a disposable circumcision anastomat. As shown in FIGS. 4-11, the disposable circumcision anastomat comprises an internal ring 2 and an external ring 1 having an opening 10. The internal ring 2 is sized and shaped to fit inside of external ring 1. The external ring 1 has a sidewall 100 that is connected to an annular blade 11. The sidewall of the external ring is provided with a retainer 7 for forming an annular retaining space with the sidewall and the annular blade. The annular retaining space is used to hold a gasket G.

FIG. 5 illustrates the cross-section of the external ring 1 of a first embodiment of a disposable circumcision anastomat. The annular blade 11, in this embodiment, comprises a dual-blade structure. The retainer 7 comprises an annular sheet 71 in the shape of a common, mechanical washer, extending inwardly from the sidewall 100 of external ring 1. The annular sheet 71 comprises an opening 710 which corresponds with the opening 10 of the external ring 1. In this embodiment, the width K1 of the annular sheet 71 is less than the width K2 of the annular blade 11. The annular sheet 71 and the blade which is located nearest with the annular sheet 71 form an annular retaining space A for securing a gasket G. The multi-blade can also use this retainer and retaining space.

Figure 11:
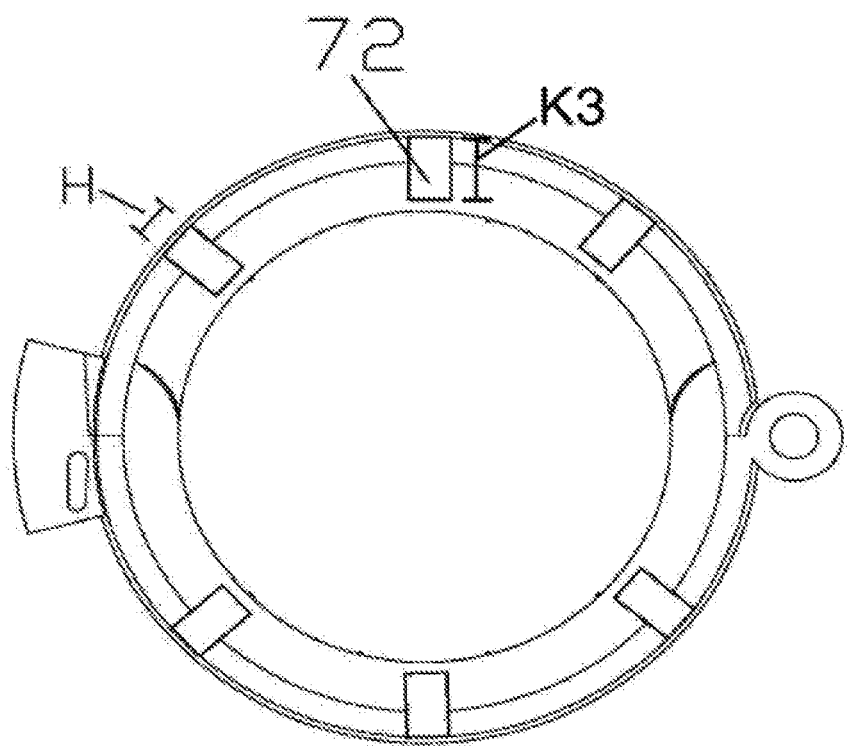
FIG. 11 is a top plan view of a second embodiment of the external ring.

FIG. 11 illustrates the external ring 2 of a second embodiment. The retainer 7 comprises tabs 72 extending inwardly from the sidewall of the external ring 1. In this embodiment, the length K3 of tab 72 is less than a width K2 of the annular blade 11. The tabs 72 and the blade which is located nearest with the annular sheet 71 form annular retaining space for retaining a gasket G. In other embodiment, the number of tabs 72 may be greater or less than the number of tabs shown in FIG. 11. Furthermore, the width H of each tab can be greater or less than what is shown in FIG. 11.

Figure 8:
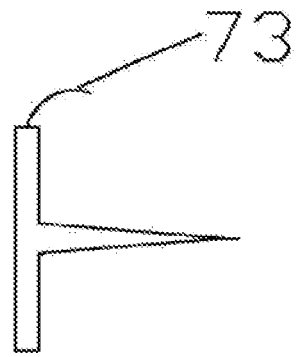
FIG. 8 illustrates a cross-section of another embodiment of the external ring.

FIG. 8 illustrates a cross-section of external ring 1 of a third embodiment. The retainer 7 comprises a series of hooks 73 extended inwardly from the sidewall of external ring 1. The hooks 73 and blade which is located nearest with the annular sheet 71 form an annular retaining space for retaining a gasket G. The hooks 73 may comprise shapes other than that shown in FIG. 8 and a greater or fewer number of hooks 73 may be used in other embodiments. The hooks 73 shown in the figure can also comprise any other structure that is able to retain a gasket G against the blade which is located nearest with the annular sheet 71.

Figure 6:
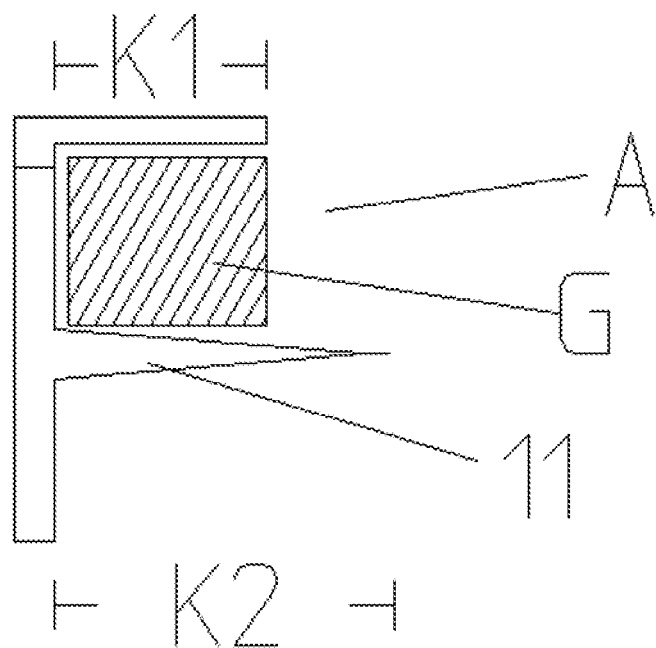
FIG. 6 illustrates a cross-section of another embodiment of the external ring used in a fourth embodiment of the disposable circumcision anastomat.
Figure 7:
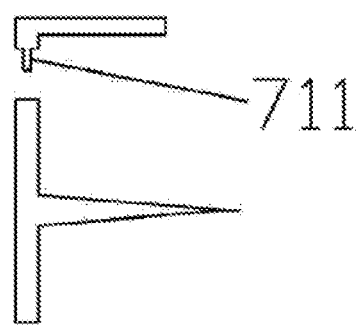
FIG. 7 is an exploded view of the external ring shown in FIG. 6.
Figure 10:
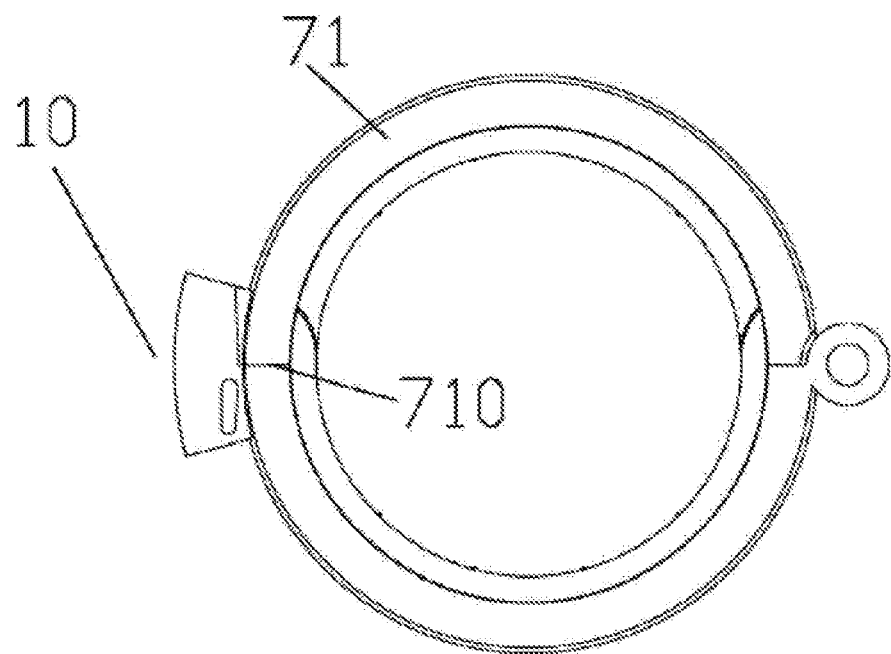
FIG. 10 is a top plan view of the first and fourth embodiments of the external ring.

FIGS. 5, 6, and 7 illustrate a cross-section of external ring 1 and three embodiments of retainer 7. In these embodiments the retainer is the annular sheet 71. In FIG. 5, the annular sheet 71 is formed as a unified structure with the annular blade 11. In FIG. 6, retainer 7 comprises an independent, removable structure. FIG. 7 shows the retainer 7 of FIG. 6 in an exploded view, comprising a male connection portion 711 for insertion into a female connection portion formed into side wall 100. The annular sheet 71 has an opening 710 at a location corresponding with opening 10 of the external ring 1. As shown in FIG. 10, the width K1 of the annular sheet is less than the width K2 of the annular blade 11, the annular sheet 71 and the adjacent annular blade 11 forming a retaining space A. The annular retaining space A is used to hold a gasket G.

Figure 9:
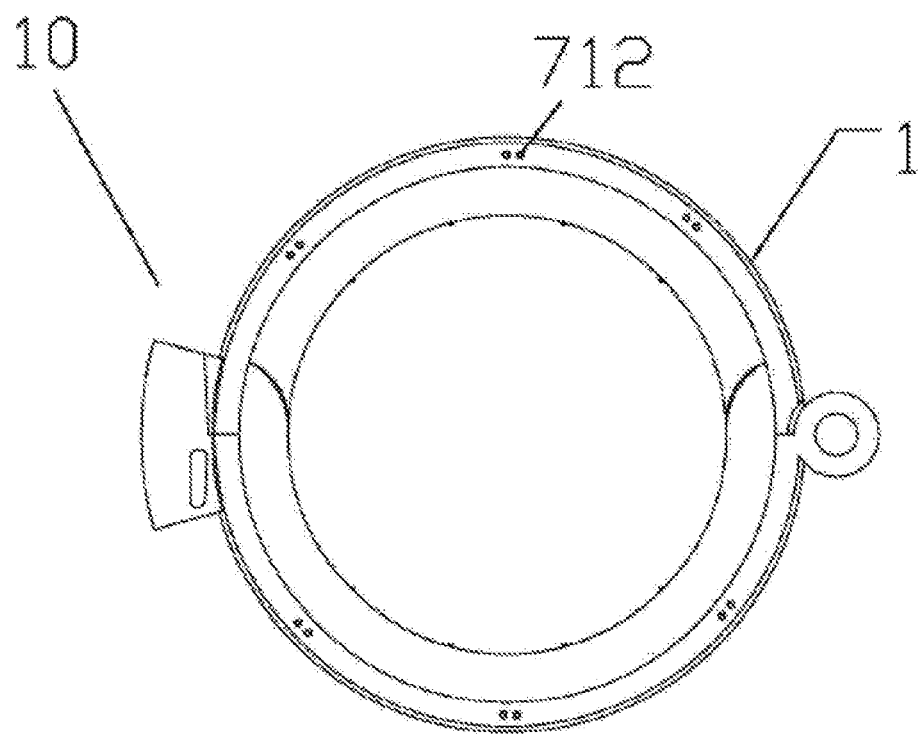
FIG. 9 illustrates a top plan view of one embodiment of the circumcision anastomat in accordance with the teachings herein showing a female connection part on the external ring.

As shown in FIG. 9, sidewall 100 of external ring 1 comprises a series of female connection portions 712 for receiving corresponding male connection portions 711 located on retainer 7. As shown in FIG. 9, the female connection portions 712 are arranged in 6 pairs around the circumference of sidewall 11, although the arrangement of female connection portions 712 may vary in other embodiments. Male connection parts 711 are arranged at corresponding locations on retainer 7. In another embodiment, the female connection portions 712 could be located on retainer 7 and the male connection portions 711 located on top of sidewall 11. The male connection portion 711 can comprise a pin, bolt, tab, or other structure that, when inserted into female connection portions 712, prevent movement of retainer 7. Female connection portions 712 comprise a hole, threaded insert, threaded hole, or any other cavity for receiving male connection portions 711. In another embodiment, female connection portions 712 comprise a threaded hole and male connection portions 712 comprise screws that are placed through holes located through retainer 7.

The ability for the retainer 7 to be removed from the external ring 1 allows a gasket G to be easily placed on top of the annular blade, then the retainer can be placed on top of the external ring sidewall 11, thus retaining the gasket G.

Figure 12:
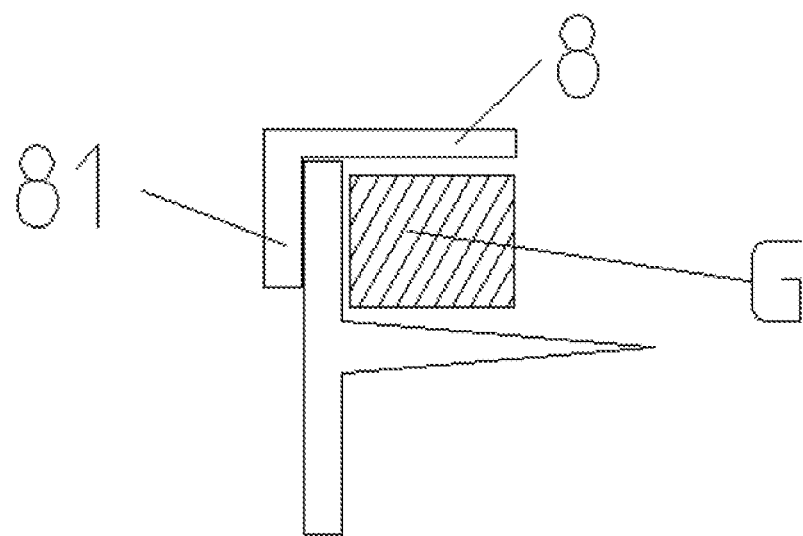
FIG. 12 is a cross-sectional view of a fifth embodiment of the external ring.

FIG. 12 is a cross-section of a fifth embodiment, showing external ring 1, annular blade 11 having two annular blades. The retainer comprises a circular sheet 8 as described with respect to retainer 7. However, in this embodiment, retainer 8 additionally comprises an annular sidewall 81 without an opening. The annular sidewall 81 comprises a diameter just large enough to be placed over sidewall 100. As in other embodiments, the width of retainer 8 is smaller than that of annular blade 11. In another embodiment, the annular sidewall 81 is connected to the sidewall 100 similar to a cover on a lunch box. The retainer 8 may be further secured to sidewall 100 by the use of threaded holes in sidewall 11, through holes in sidewall 81, and screws to hold the structures together.

Figure 13:
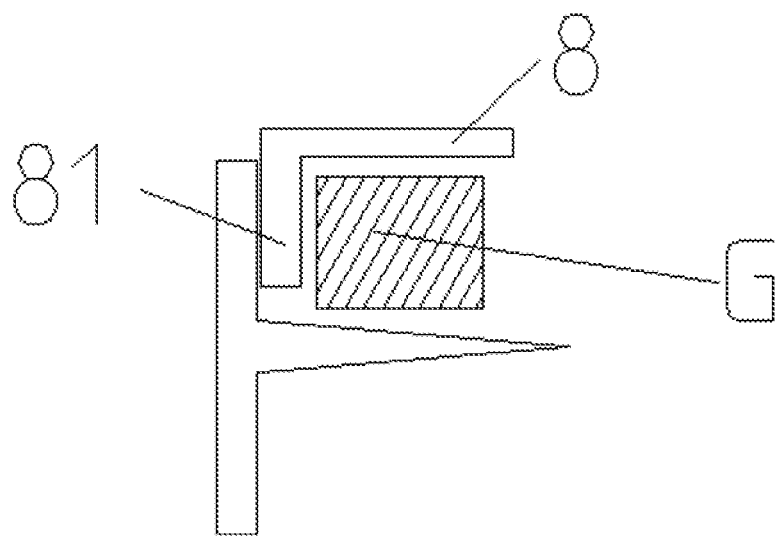
FIG. 13 illustrates the cross-section of a sixth embodiment of the external ring.

FIG. 13 is a cross-section of a sixth embodiment, wherein the annular sidewall 81 lies within the interior side of side wall 100. Both the annular sidewall and the sidewall of the external ring comprise screw threads, the annular sidewall and the external ring are joined together with screws placed into the screw threads.

In one embodiment, a gasket G can form part of the disposable circumcision anastomat or it may be purchased as an accessory. The gasket G can be made of absorbent materials so as to absorb various drugs. The drugs can comprise disinfectant drugs, anesthetic drugs or other drugs. In another embodiment, the gasket G comprises a common rubber gasket to prevent bacteria from forming at the surgical site.

The gasket G may also comprise non-woven fabrics, cotton, a sponge, or other absorbent material, with or without drugs.

In summary, the present invention comprises a disposable circumcision anastomat comprising an annular retaining space that retains a gasket G, so as to make the circumcision anastomat safer and reduce pain experienced by patients after surgery. It can be used on any operational circumcising tools of any structure.

With respect to the above description, it is to be realized that the optimum dimensional relationships of the various components include variations in size, materials, shape, form, function and manner of operation, assembly and use, and are deemed readily apparent and obvious to one skilled in the art. All equivalent relationships to those illustrated in the drawings and described in the specification are intended to be encompassed by the embodiments described herein. Therefore, the foregoing is considered as illustrative only of the principles and descriptions provide herein. Further, since numerous modifications and changes may be contemplated by those skilled in the art, it is not desired to limit the embodiments described herein to the exact construction and operation shown and described, and accordingly, all suitable modifications and equivalents may be resorted to, falling within the scope of the present disclosure.

We claim:

1. A disposable circumcision apparatus comprising:
   an uninterrupted internal ring;
   an external ring with an opening for concentric placement around the internal ring, the external ring comprising a sidewall that is connected to at least one blade;
   a retainer separately set with the external ring and located around a top edge of the external ring forming an annular retaining space between the retainer, an inner wall of the external ring and the blade; and
   a gasket positioned between the retainer and the blade;
   wherein the blade and the external ring are an integrated structure.

2. An apparatus as claimed in claim 1, wherein: the retainer comprises an annular sheet extended inwardly from the sidewall of the external ring, the annular sheet equipped with a second opening which corresponds with the opening on the external ring, and a width of the annular sheet is smaller than a width of the blade.

3. An apparatus as claimed in claim 1, wherein: the retainer comprises a plurality of strips extended inwardly from the sidewall of the external ring, wherein a width of each of the plurality of strips is smaller than a width of the blade, wherein the plurality of strips, an inner wall of the external ring and the blade located nearest with the plurality of strips form an annular holding space for holding the gasket.

4. An apparatus as claimed in claim 1, wherein: the retainer comprises a plurality of hooks extended inwardly from the sidewall of the external ring, wherein the plurality of hooks, the inner wall of the of the external ring and the blade located nearest with the plurality of strips form an annular holding space for holding the gasket.

5. An apparatus as claimed in claim 1, wherein: the retainer is connected to the external ring via a joint structure.

6. An apparatus as claimed in claim 5, wherein: the joint structure comprises a plurality of male connection parts arranged at the retainer and a plurality of female connection parts arranged on a top edge of the external ring, or a female connection part arranged at the retainer and a male connection part arranged on the top edge of the external ring.

7. An apparatus as claimed in claim 6, wherein: the plurality of male connection parts are a plurality of pins and the female connection parts are a plurality of holes corresponding to the plurality of pins.

8. An apparatus as claimed in claim 1, wherein: the retainer comprises a circular sheet, wherein the circular sheet extends outwardly to form an extending part to fix the circular onto the external ring, wherein the circular sheet and the extending part form a cover which covers an outside circumference of the sidewall of the external ring, wherein a width of the circular sheet is smaller than a width of the blade; the circular sheet and the extending part are an integrated structure.

9. An apparatus as claimed in claim 8, wherein: an inner wall of the extending part comprises a plurality of screw threads; an outer wall of the external ring comprises a plurality of screw threads corresponding to the plurality of screw threads of the extending part;
   wherein the circular sheet is jointed with the external ring through the plurality of screw threads.

10. An apparatus as claimed in claim 1, wherein: the gasket is made of absorbent materials.

11. An apparatus as claimed in claim 10, wherein: the gasket is made of non-woven fabrics, cotton, or a sponge.

12. An apparatus as claimed in claim 11, further comprising: an anesthetic drug retained by the gasket.

13. The apparatus as claimed in claim 1, wherein: the retainer comprises a circular sheet, wherein the circular sheet extends outwardly to form an extending part, the extending part is connected with an inner wall of the external ring; a width of the circular sheet is smaller than a width of the blade; the circular sheet and the extending part are an integrated structure.

14. The apparatus as claimed in claim 13, wherein an outer wall of the extending part comprises a plurality of screw threads; an inner wall of the external ring comprises a plurality of screw threads corresponding to the plurality of screw threads of the extending part; the circular sheet is jointed with the external ring through the plurality of screw threads.

* * * * *